(12) United States Patent
Wang et al.

(10) Patent No.: US 8,349,275 B2
(45) Date of Patent: Jan. 8, 2013

(54) MICROFLUIDIC DEVICE WITH MICROSTRUCTURE, AND SENSING SYSTEM AND METHOD USING SAME

(75) Inventors: Shau-Chun Wang, Chiayi (TW); Lai-Kwan Chau, Chiayi (TW); Wen-Hsin Hsieh, Taipei (TW); Chia-Yu Lee, Tainan (TW)

(73) Assignee: National Chung Cheng University, Chia-Yi (TW)

( * ) Notice: Subject to any disclaimer, the term of this patent is extended or adjusted under 35 U.S.C. 154(b) by 452 days.

(21) Appl. No.: 12/359,080

(22) Filed: Jan. 23, 2009

(65) Prior Publication Data

US 2009/0190877 A1    Jul. 30, 2009

Related U.S. Application Data

(60) Provisional application No. 61/006,653, filed on Jan. 25, 2008.

(51) Int. Cl.
*G01N 21/62* (2006.01)
*G01N 33/53* (2006.01)

(52) U.S. Cl. ............. 422/503; 422/82.05; 436/172

(58) Field of Classification Search ............ 204/450; 422/82.08, 502, 503; 436/172
See application file for complete search history.

(56) References Cited

U.S. PATENT DOCUMENTS

| 6,086,243 | A  | * | 7/2000 | Paul et al. | 366/273 |
|---|---|---|---|---|---|
| 7,483,140 | B1 | * | 1/2009 | Cho et al. | 356/445 |
| 7,691,244 | B2 | * | 4/2010 | Levitan et al. | 204/450 |
| 2003/0007715 | A1 | * | 1/2003 | Loock et al. | 385/12 |
| 2004/0130723 | A1 | * | 7/2004 | Yager et al. | 356/445 |
| 2007/0080062 | A1 | * | 4/2007 | Harnett et al. | 204/450 |
| 2007/0115469 | A1 | * | 5/2007 | Ebstein | 356/301 |

* cited by examiner

*Primary Examiner* — In Suk Bullock
*Assistant Examiner* — Paul Hyun
(74) *Attorney, Agent, or Firm* — WPAT, P.C.; Anthony King

(57) ABSTRACT

A microfluidic device with microstructure includes a channel for accommodating an electrolytic solution therein and at least one microstructure formed in the channel. When an alternating-current signal is input to the microfluidic device so that a surface of the microstructure is polarized by a generated electric field, ions having polarity reverse to that of an electrolytic solution will migrate to the surface of the microstructure to form a field-induced electrical double layer to result in electro-osmotic flows at the corners at two sides of the microstructure, which causes formation of relatively fierce circular vortices in the solution. A sensing system and a sensing method using the microfluidic device with microstructure are also disclosed.

29 Claims, 7 Drawing Sheets

Microfluidic device 1

MICROFLUIDIC DEVICE WITH MICROSTRUCTURE, AND SENSING SYSTEM AND METHOD USING SAME

FIELD

The present invention relates to a microfluidic device, and more particularly to a microfluidic device having at least one microstructure formed in a channel thereof. The present invention also relates to a sensing system and a sensing method using the microfluidic device with microstructure.

BACKGROUND

Currently, most of the biochips are used to carry out biochemical analysis reactions or some part of the reactions. Compared to conventional analytical methods, biochips have the advantages of easy to operate, requiring less sample volume, allowing different reactions to take place at the same time, mass-producible, quick reaction speed, etc. A microfluidic device is one of many forms that implement the biochips. In a microfluidic device, channels, reaction chambers, mixers, and valves are provided on a substrate thereof to control flowing direction, reaction time, mixing ratio, etc. of different fluids on a chip, so as to achieve the purpose of controlling the reaction process. However, when a solution with a relatively high molecular weight solutes is supplied into the microfluidic device, the solutes diffuse in the channel at a relatively slow speed and accordingly, a relatively long sensing signal readout time is needed. Therefore, it is important to develop a way to speed up the migration of the solutes in the channels on a microfluidic device.

SUMMARY

A primary object of the present invention is to provide a microfluidic device with microstructure and sensing system and method using same, so as to speed up the mass transfer of solutes in a channel of the microfluidic device.

Another object of the present invention is to provide a microfluidic device with microstructure and sensing system and method using same, so as to accelerate the binding dynamics between a solute analyte and a functional group immobilized on a metal nanoparticle layer.

A further object of the present invention is to provide a microfluidic device with microstructure and sensing system and method using same, so as to shorten the time needed for reading out a sensing signal.

To achieve the above and other objects, the microfluidic device with microstructure according to the present invention includes a base, a sensing element, and two electrodes. The base is provided with a channel for accommodating a solution therein, and the channel has a sensing section, in which at least one microstructure is provided. The sensing element is arranged in the sensing section and has a noble metal nanoparticle layer coated on an outer surface thereof. The two electrodes are electrically and respectively connected to two ends of the sensing section.

In the present invention, the microstructure can be formed by way of ultraviolet-lithography galvanoformung abformung (UV-LIGA), printing, or ablating, with or without combining injection molding.

In the present invention, the microstructure has a height between 10 μm and 1000 μm, and more preferably between 10 μm and 100 μm.

In the present invention, the noble metal nanoparticle layer contains gold nanoparticles, silver nanoparticles, or other functionalized noble metal nanoparticles.

In the present invention, the two electrodes receive an alternating-current (AC) signal, which leads to formation of relatively fierce vortices in the solution at corners of the microstructure.

To achieve the above and other objects, the sensing system according to the present invention includes a microfluidic device, a signal generator, a light emitting device, a solution supplying device, and a light detecting device. The microfluidic device includes a base, a sensing element, and two electrodes. The base is provided with a channel having a sensing section, in which at least one microstructure is provided. The sensing element is arranged in the sensing section and has a noble metal nanoparticle layer coated on an outer surface thereof. The two electrodes are electrically and respectively connected to two ends of the sensing section. The signal generator is adapted to generate an AC signal to the two electrodes. The light emitting device is adapted to provide an incident light for coupling into the sensing element. The sensing element may be an optical fiber element or a planar waveguide component. The solution supplying device is used to supply an analyte-containing solution into the channel. And, the light detecting device is adapted to detect an emergent light from the optical fiber element.

The light detecting device is also adapted to measure from the emergent light changes in a localized plasmon resonance (LPR) signal. The sensing element may be an optical fiber element or a planar waveguide component. And, the signal can be generated by any evanescent wave-based sensing means.

To achieve the above and other objects, the sensing method according to the present invention is applicable to a microfluidic device that includes a channel with a sensing section, a sensing element arranged in the sensing section, and two electrodes electrically and respectively connected to two ends of the sensing section. The sensing method includes the following steps: (1) forming at least one microstructure in the sensing section; (2) preparing a noble metal nanoparticle layer and coating the same on an outer surface of the sensing element; (3) supplying an analyte-containing solution into the channel; (4) providing an incident light and coupling the same into the sensing element; (5) inputting an alternating-current (AC) signal via the two electrodes; and (6) detecting an emergent light from the sensing element. The sensing element may be an optical fiber element or a planar waveguide component, and the signal can be generated by any evanescent wave-based sensing means.

In the step of detecting the emergent light, changes in a localized plasmon resonance (LPR) signal is measured.

With these and other objects, advantages, and features of the invention that may become hereinafter apparent, the nature of the invention may be more clearly understood by reference to the detailed description of the invention, the embodiments and to the several drawings herein.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

Exemplary embodiments of the present invention are described herein in the context of microfluidic device with microstructure, and sensing system and method using same.

Those of ordinary skilled in the art will realize that the following detailed description of the exemplary embodiment(s) is illustrative only and is not intended to be in any way limiting. Other embodiments will readily suggest themselves to such skilled persons having the benefit of this disclosure. Reference will now be made in detail to implementations of the exemplary embodiment(s) as illustrated in the accompanying drawings. The same reference indicators will be used throughout the drawings and the following detailed description to refer to the same or like parts.

Figure 1:
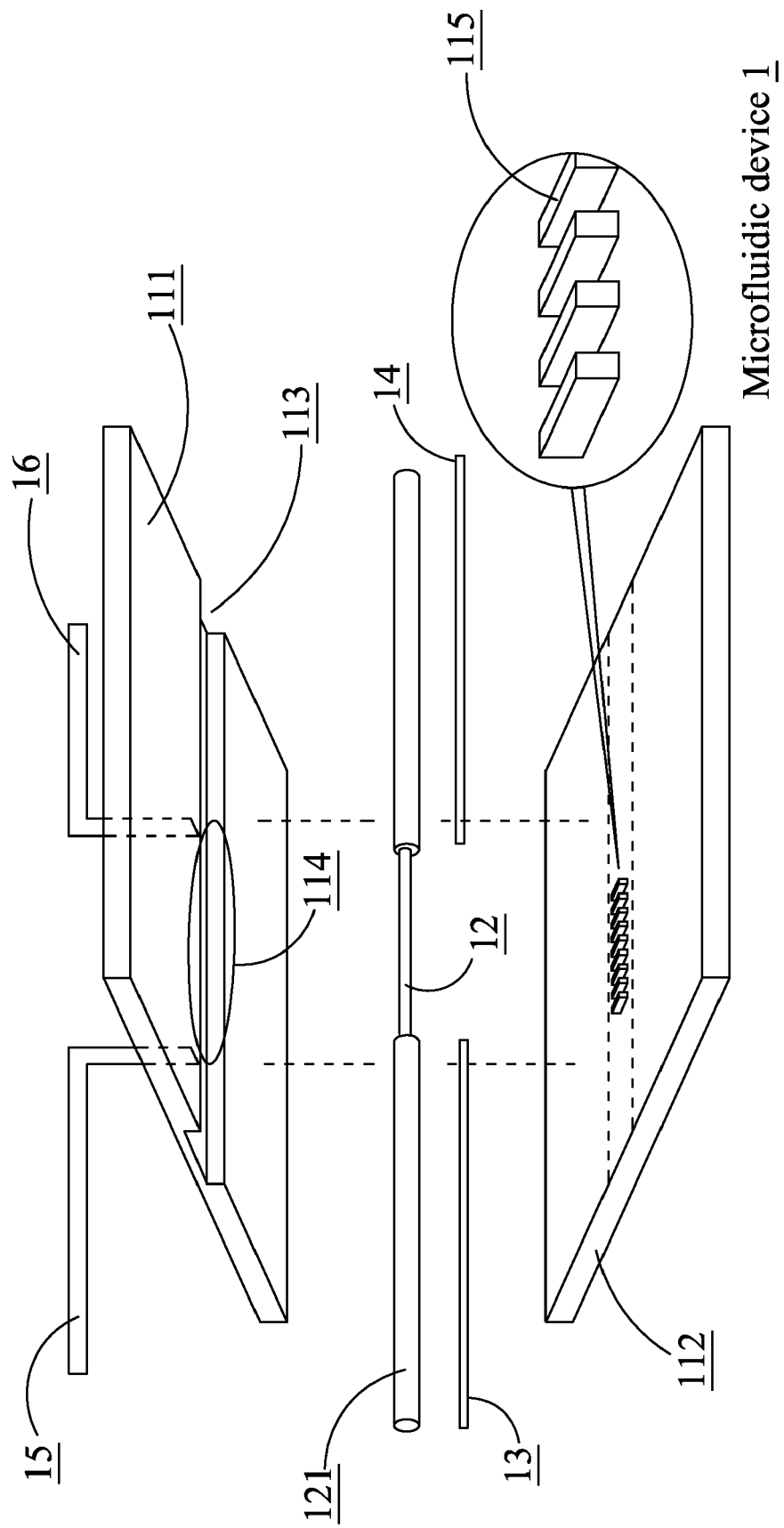
FIG. 1 is an exploded perspective view of an embodiment of a microfluidic device with microstructure according to the present invention.

Please refer to FIG. 1 that is an exploded perspective view of an embodiment of a microfluidic device with microstructure according to the present invention. As shown, the microfluidic device, which is generally denoted by reference numeral 1, includes a base, an optical fiber element 12, two electrodes 13, 14, a solution inlet tube 15, and a solution outlet tube 16. The base has a channel for accommodating a solution therein. In the illustrated embodiment, the base is composed of an upper substrate 111 and a lower substrate 112. The upper substrate 111 is provided with a band-like groove 113, such that the band-like groove 113 forms the channel when the upper substrate 111 and the lower substrate 112 are assembled together. Since the channel for the microfluidic device is known in the art, it is not discussed in details herein. Preferably, the upper and the lower substrate 111, 112 are made of a plastic material.

A section of the band-like groove 113 is defined as a sensing section 114, and a portion of the lower substrate 112 corresponding to the sensing section 114 has at least one microstructure 115. Thus, when the upper substrate 111 and the lower substrate 112 are assembled together, the at least one microstructure 115 is located in the sensing section 114. The microstructure 115 is an embossed structure having a length or width between 0.1 mm and 1.0 mm, and can be a relief-like structure or a wedge-shape microstructure having a height between 10 µm and 1000 µm, and more preferably between 10 µm and 100 µm. The microstructure 115 is preferably formed on the lower substrate 112 by way of ultraviolet-lithography galvanoformung abformung (UV-LIGA), printing, or ablating, with or without combining injection molding.

Figure 2:
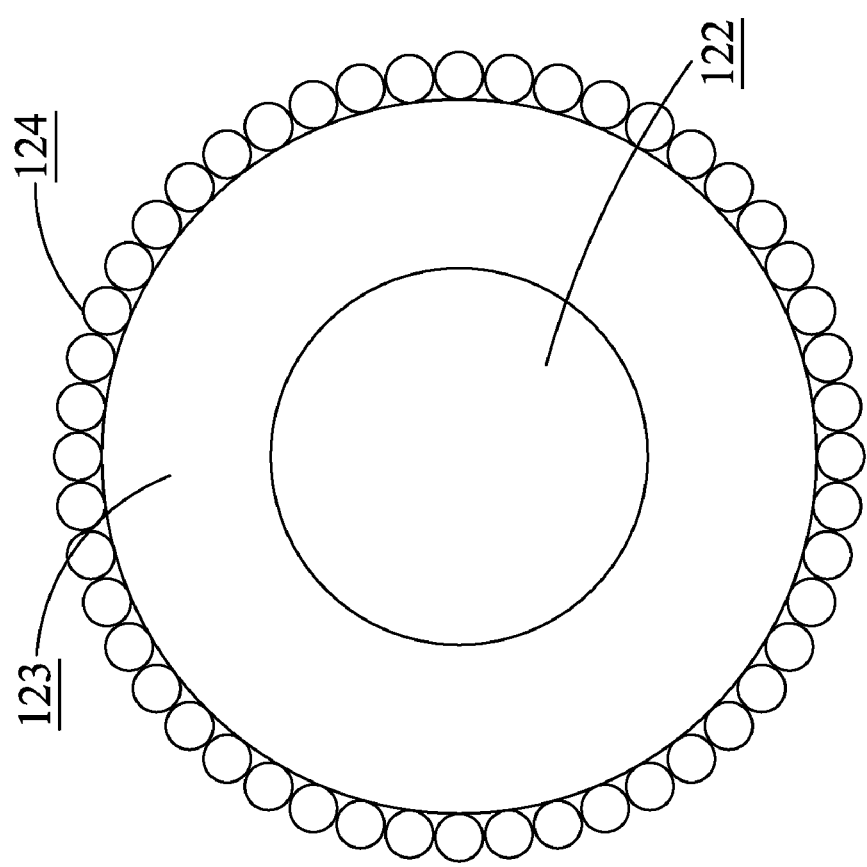
FIG. 2 is a cross-sectional view of an optical fiber element for the microfluidic device of the present invention.

The optical fiber element 12 is arranged in the sensing section 114 and has a noble metal nanoparticle layer 124 coated on an outer surface thereof. In the illustrated embodiment, the optical fiber element 12 is a section of an optical fiber 121 with a portion of a surface protective layer 124 and a portion of a cladding layer 123 thereof being stripped therefrom, so that only a fiber core 122 and the remaining part of the cladding layer 123 are remained at the optical fiber element 12 with the noble metal nanoparticle layer 124 coated on the outer surface of the optical fiber element 12, as shown in FIG. 2. Preferably, the noble metal nanoparticle layer 124 contains gold nanoparticles, silver nanoparticles, or other functionalized noble metal nanoparticles, such as gold nanoparticles with biotin functional group. Alternatively, the optical fiber element 12 can be replaced with a planar waveguide component, depending on actual need.

The electrodes 13, 14 are electrically and respectively connected to two ends of the sensing section 114 for sending a received electric signal, such as an alternating-current (AC) signal, to the sensing section 114. In the illustrated embodiment, the electrodes 13, 14 can be inserted along the optical fiber 121 to a lower side of the optical fiber element 12 to approach to the sensing section 114. Alternatively, two small holes can be drilled near two ends of the sensing section 114, so that the electrodes 13, 14 can be respectively inserted thereinto. In the illustrated embodiment, the solution inlet tube 15 and the solution outlet tube 16 are extended through the upper substrate 111 for supplying a solution to the sensing section 114 and extracting the solution from the sensing section 114, respectively.

Figure 3:
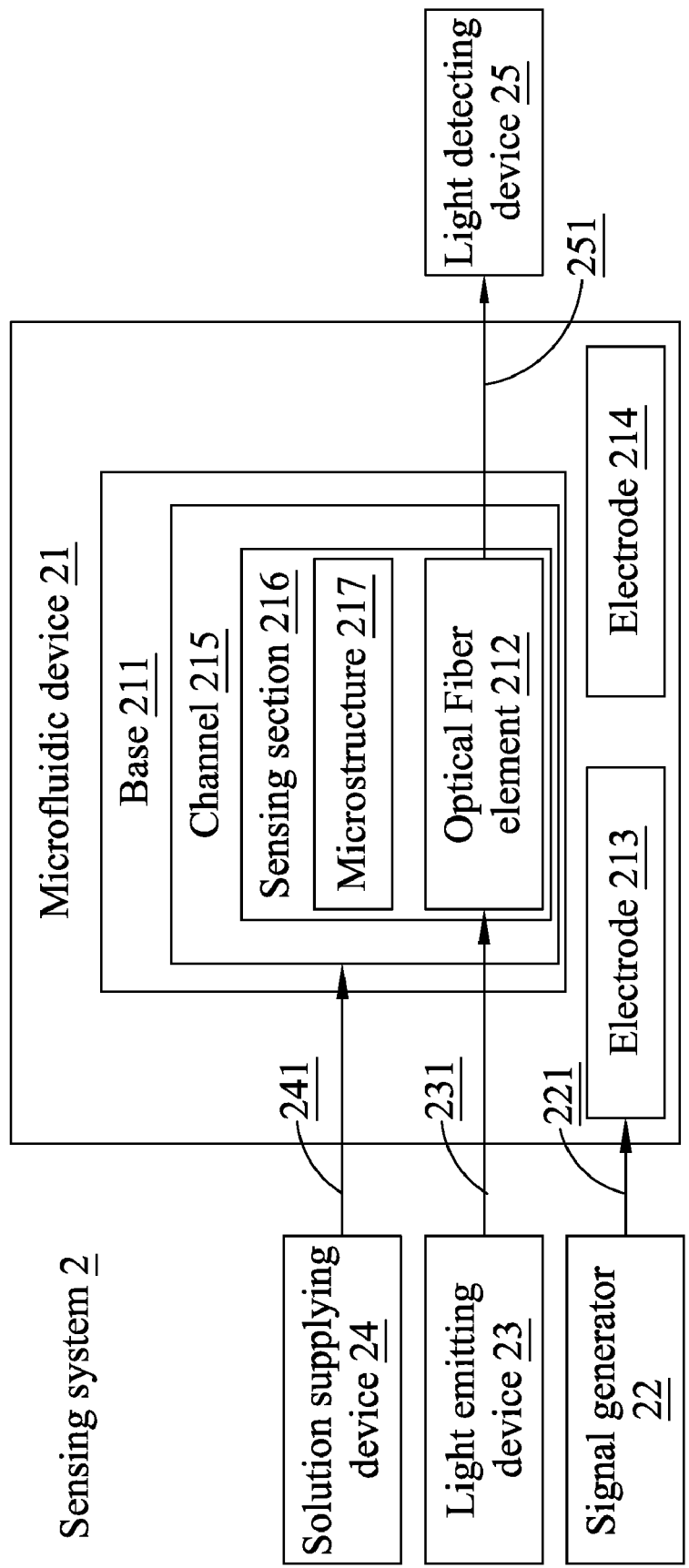
FIG. 3 is a block diagram of an embodiment of a sensing system according to the present invention.

Please refer to FIG. 3 that is a block diagram of an embodiment of a sensing system 2 according to the present invention. As shown, the sensing system 2 includes a microfluidic device 21, a signal generator 22, a light emitting device 23, a solution supplying device 24, and a light detecting device 25. The microfluidic device 21 includes a base 211, an optical fiber element 212, and two electrodes 213, 214. The base 211 is provided with a channel 215 having a sensing section 216, and the sensing section 216 has at least one microstructure 217 arranged therein. The optical fiber element 212 is arranged in the sensing section 216 and is provided on an outer surface thereof with a noble metal nanoparticle layer. The two electrodes 213, 214 are electrically and respectively connected to two ends of the sensing section 216. It is noted the microfluidic device 21 has a structure similar to that shown in FIG. 1. Therefore, the microfluidic device 21 is only shown as a block diagram without being discussed in details herein.

The light emitting device 23 is adapted to provide an incident light 231 for coupling into the optical fiber element 212. Preferably, the incident light 231 is a monochromatic light, a narrow-band light, or a white light. The solution supplying device 24 is adapted to supply an analyte-containing solution 241 into the channel 215. The signal generator 22 is adapted to generate an AC signal 221 to the two electrodes 213, 214. The light detecting device 25 is adapted to detect an emergent light 251 from the optical fiber element 212, so as to measure from the emergent light 251 changes in a localized plasmon resonance (LPR) signal.

Figure 4:
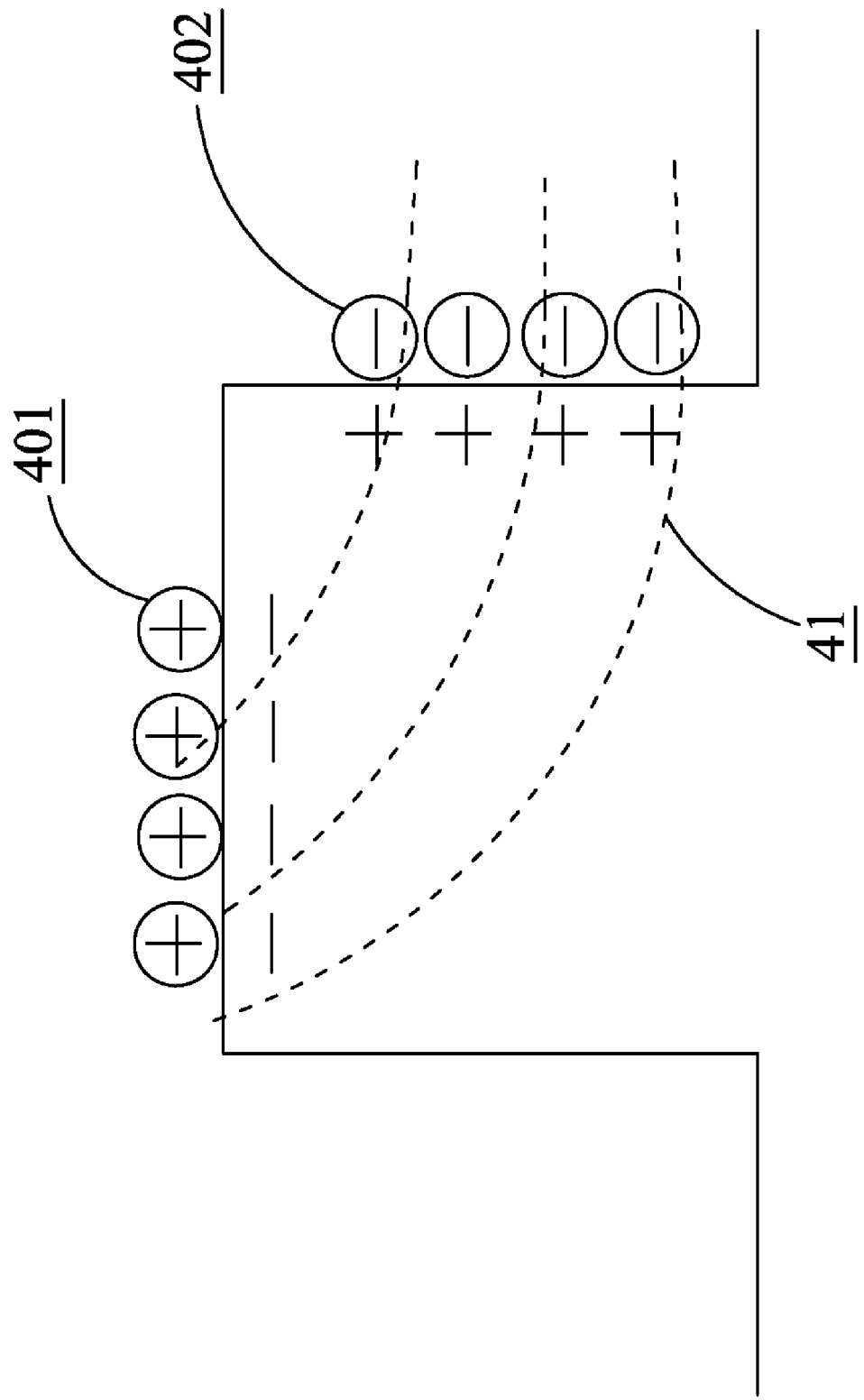
FIG. 4 shows electrical field changes around a microstructure of the microfluidic device of the present invention.

FIG. 4 shows electrical field changes around a microstructure of the microfluidic device of the present invention. In the illustrated embodiment, the microstructure is a wedge-shape microstructure. When an electric signal is input to the sensing section 216, one side of the sensing section 216 as shown at the left side of the drawing may have a higher voltage level while another side of the sensing section 216 as shown at the right side of the drawing may have a lower voltage level, or vice versa, so that an external electric field is generated in the sensing section 216. When a surface of the wedge-shape microstructure has been polarized by the electric field, ions

401, 402 having polarity reverse to that of an electrolyte solution will migrate to the surface of the wedge-shape microstructure to form a field-induced electrical double layer. When an externally applied electric field drives electric charges adsorbed onto the electrical double layer, electro-osmosis occurs. When a high-frequency AC field is used to quickly change the electric field polarity, the induced charges are not neutralized but can maintain the electrical double layer. Therefore, the corners at two sides of the wedge-shape microstructure have a relatively high normal field 41, which causes formation of relatively fierce circular vortices in the solution 241 to thereby speed the transfer of the solution 241 in the sensing section 216 and accelerate the binding dynamics between the solute analyte and the functionalized noble metal nanoparticles immobilized on the metal nanoparticle layer, allowing the LPR signal to become stable more quickly and thereby shortening the time needed for reading out the sensing signal.

Figure 5:
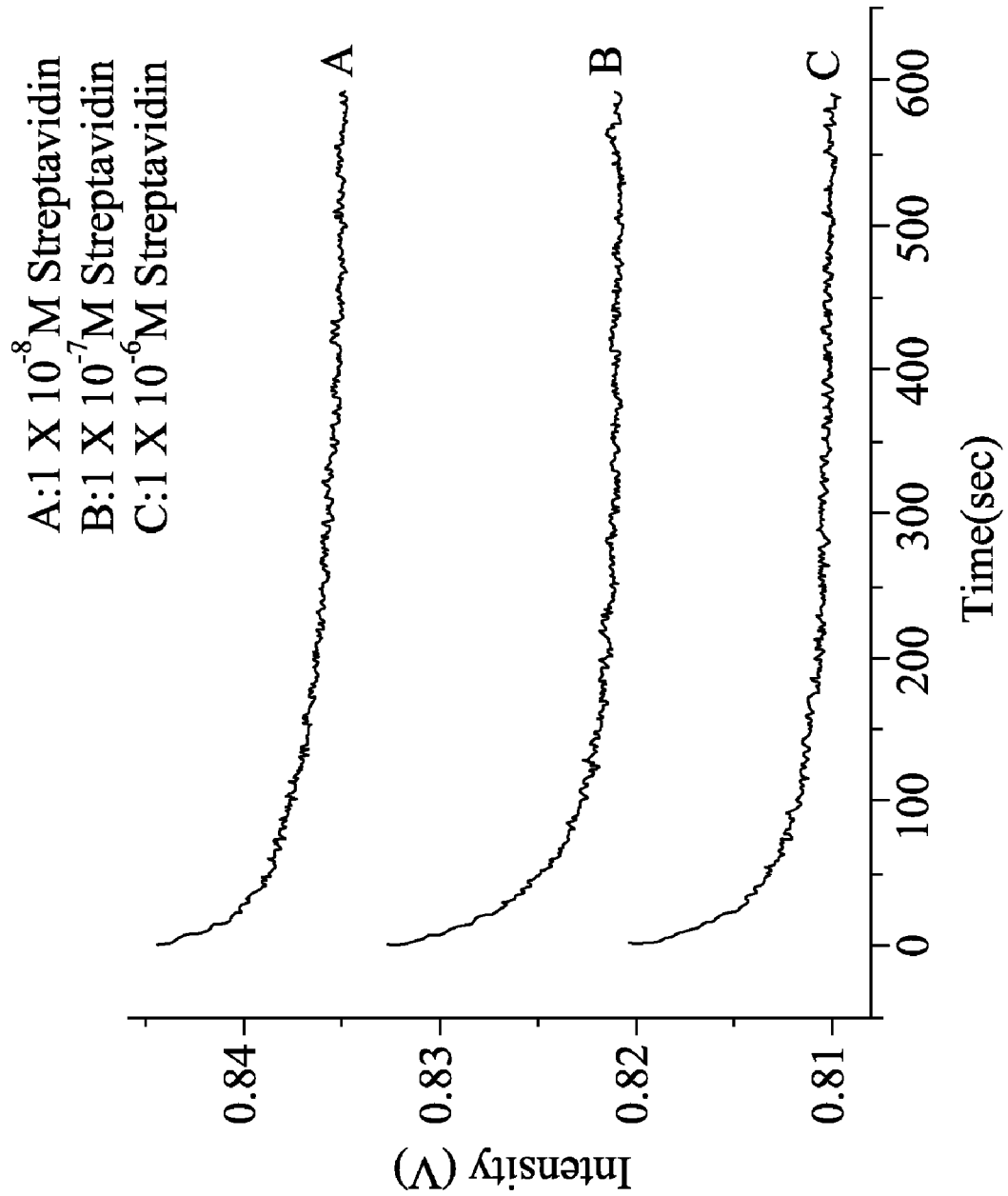
FIG. 5 is a graph showing time sequence signals measured using a microfluidic device without microstructure.
Figure 6:
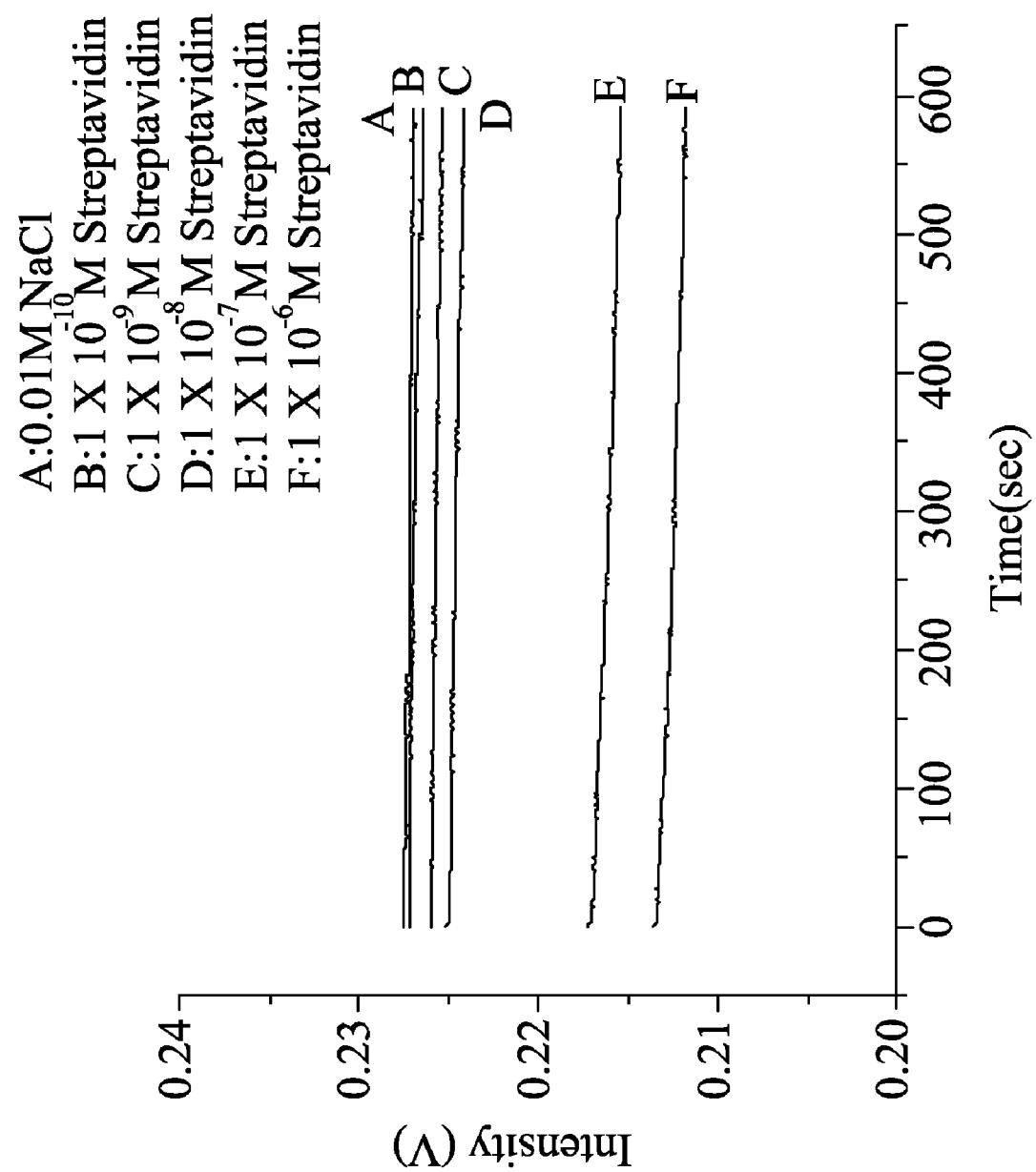
FIG. 6 is a graph showing time sequence signals measured using a microfluidic device with microstructure according to the present invention.

FIG. 5 is a graph showing time sequence signals measured using a microfluidic device without microstructure, and FIG. 6 is a graph showing time sequence signals measured using a microfluidic device with microstructure according to the present invention. Please refer to FIGS. 5 and 6 at the same time. The curves shown in the graphs are time sequence signals at the time streptavidin in a 0.01M background electrolytic solution (NaCl) is bonded to gold nanoparticles with biotin functional group on a section of an optical fiber that is partially stripped. As can be observed, compared to the curves in FIG. 5, the curves in FIG. 6 are relatively flat due to the AC-induced electro-osmosis that speeds up the binding dynamics. Therefore, when the externally applied electric field is switched off, the signal balancing is reached at the same time. On the other hand, when the microfluidic device does not include any microstructure, the induced electro-osmosis is suppressed. That is why the sensing signals shown in FIG. 5 will become steady only when the externally applied electric field has been switched off for more than 200 seconds. From the above description, it can be understood the use of alternating current field to induce electro-osmosis can speed up the biomolecular binding dynamics to thereby shorten the signal readout time.

Figure 7:
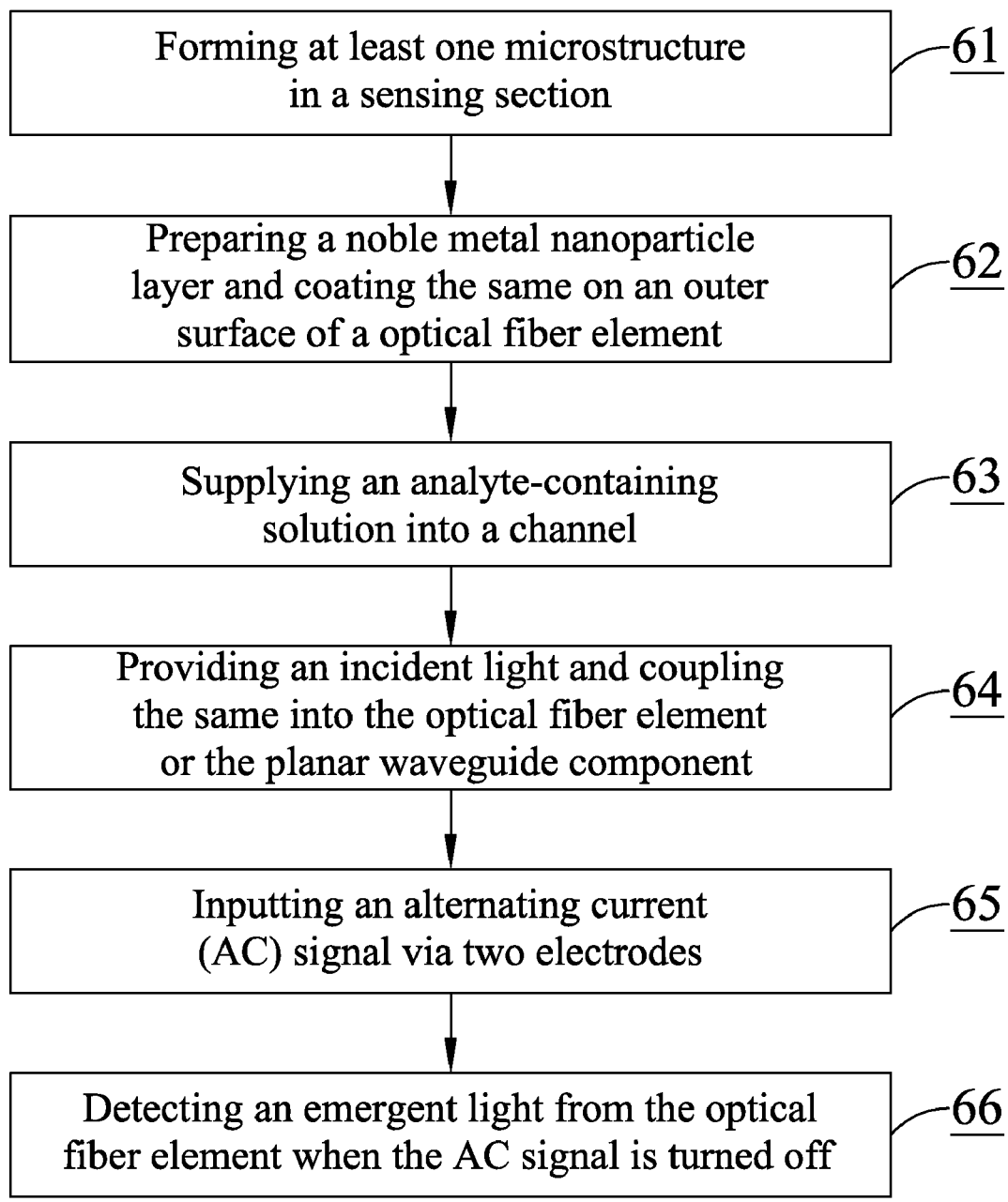
FIG. 7 is a flowchart showing the steps included in a sensing method according to an embodiment of the present invention.

Please refer to FIG. 7 that is a flowchart showing the steps included in a sensing method according to an embodiment of the present invention. The sensing method is applicable to a microfluidic device that includes a channel having a sensing section, an optical fiber element arranged in the sensing section, and two electrodes electrically and respectively connected to two ends of the sensing section. The sensing method includes the following steps:

Step 61: Forming at least one microstructure in the sensing section; for example, the microstructure can be a relief-like structure or a wedge-shape microstructure formed in the sensing section by way of ultraviolet-lithography galvanoformung abformung (UV-LIGA), printing, or ablating, with or without combining injection molding;

Step 62: Preparing a noble metal nanoparticle layer and coating the same on an outer surface of the optical fiber element;

Step 63: Supplying an analyte-containing solution into the channel;

Step 64: Providing an incident light and coupling the same into the optical fiber element or the planar waveguide component;

Step 65: Inputting an alternating-current (AC) signal via the two electrodes; and Step 66: Detecting an emergent light from the optical fiber element when the AC signal is turned off.

The present invention has been described with some preferred embodiments thereof and it is understood that many changes and modifications in the described embodiments can be carried out without departing from the scope and the spirit of the invention that is intended to be limited only by the appended claims.

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope of all such changes and modifications as are within the true spirit and scope of the exemplary embodiment(s) of the present invention.

What is claimed is:

1. A microfluidic device with microstructure, comprising:
a base having a channel for accommodating a solution therein, the channel including a sensing section, and the sensing section having at least one microstructure, which is consisting of a plastic material without surface electric charge, arranged therein, wherein a plurality of ions migrate to a surface of the at least one microstructure to form a field-induced electrical double layer when the surface of the microstructure has been polarized by an electric field, wherein the base comprises an upper substrate and a lower substrate, one of the upper substrate and the lower substrate being formed with a band-like groove, such that the band-like groove forms the channel when the upper substrate and the lower substrate are assembled together, wherein the upper and the lower substrate are made of the plastic material;
a sensing element being arranged in the sensing section, the sensing element being provided on an outer surface thereof with a noble metal nanoparticle layer; and
two electrodes being electrically and respectively connected to two ends of the sensing section and receiving a high-frequency alternating-current (AC) signal to make a plurality of induced charges not neutralized and the field-induced electrical double layer maintained.

2. The microfluidic device with microstructure as claimed in claim 1, wherein the sensing element is selected from the group consisting of an optical fiber element and a planar waveguide component.

3. The microfluidic device with microstructure as claimed in claim 2, wherein the optical fiber element is a section of an optical fiber with a portion of a surface protective layer and a portion of a cladding layer thereof being stripped therefrom.

4. The microfluidic device with microstructure as claimed in claim 1, wherein the microstructure is an embossed structure having a length or width between 0.1 mm and 1.0 mm.

5. The microfluidic device with microstructure as claimed in claim 4, wherein the embossed structure is selected from the group consisting of a relief-like structure and a wedge-shape microstructure.

6. The microfluidic device with microstructure as claimed in claim 1, wherein the microstructure is formed by a manner selected from the group consisting of ultraviolet-lithography galvanoformung abformung (UV-LIGA), printing, and ablating, with or without combining injection molding.

7. The microfluidic device with microstructure as claimed in claim 1, wherein the microstructure has a height between 10 μm and 1000 μm.

8. The microfluidic device with microstructure as claimed in claim 1, wherein the noble metal nanoparticle layer contains a type of noble metal nanoparticles selected from the group consisting of gold nanoparticles, silver nanoparticles, and other functionalized noble metal particles.

9. The microfluidic device with microstructure as claimed in claim 1, wherein the two electrodes receive a high-frequency alternating-current (AC) signal, which leads the formation of circular vortices in the solution at corners of the microstructure.

10. A sensing system, comprising:
a microfluidic device with microstructure, comprising:
  a base having a channel for accommodating a solution therein, the channel including a sensing section, and the sensing section having at least one microstructure, which is consisting of a plastic material without surface electric charge, arranged therein, wherein a plurality of ions migrate to a surface of the at least one microstructure to form a field-induced electrical double layer when the surface of the microstructure has been polarized by an electric field, wherein the base comprises an upper substrate and a lower substrate, one of the upper substrate and the lower substrate being formed with a band-like groove, such that the band-like groove forms the channel when the upper substrate and the lower substrate are assembled together, wherein the upper and the lower substrate are made of the plastic material;
  a sensing element being arranged in the sensing section, the sensing element being provided on an outer surface thereof with a noble metal nanoparticle layer; and
  two electrodes being electrically and respectively connected to two ends of the sensing section and receiving a high-frequency alternating-current (AC) signal to make a plurality of induced charges not neutralized and the field-induced electrical double layer maintained;
  a signal generator being adapted to generate an AC signal to the two electrodes;
  a light emitting device being adapted to provide an incident light for coupling into the sensing element;
  a solution supplying device being adapted to supply an analyte-containing solution into the channel; and
  a light detecting device being adapted to detect an emergent light from the sensing element.

11. The sensing system as claimed in claim 10, wherein the sensing element is selected from the group consisting of an optical fiber element and a planar waveguide component.

12. The sensing system as claimed in claim 11, wherein the optical fiber element is a section of an optical fiber with a portion of a surface protective layer and a portion of a cladding layer thereof being stripped therefrom.

13. The sensing system as claimed in claim 10, wherein the microstructure is an embossed structure having a length or width between 0.1 mm and 1.0 mm.

14. The sensing system as claimed in claim 13, wherein the embossed structure is selected from the group consisting of a relief-like structure and a wedge-shape microstructure.

15. The sensing system as claimed in claim 10, wherein the microstructure is formed by a manner selected from the group consisting of ultraviolet-lithography galvanoformung abformung (UV-LIGA), printing, and ablating, with or without combining injection molding.

16. The sensing system as claimed in claim 10, wherein the microstructure has a height between 10 μm and 1000 μm.

17. The sensing system as claimed in claim 10, wherein the noble metal nanoparticle layer contains a type of noble metal nanoparticles selected from the group consisting of gold nanoparticles, silver nanoparticles, and other functionalized noble metal particles.

18. The sensing system as claimed in claim 10, the two electrodes receive a high-frequency alternating-current (AC) signal, which leads the formation of circular vortices in the solution at corners of the microstructure.

19. The sensing system as claimed in claim 10, wherein the light detecting device is adapted to measure from the emergent light changes in a signal of localized plasmon resonance on the sensing element, and the signal can be generated by any evanescent wave-based sensing means.

20. A sensing method applicable to a microfluidic device, the microfluidic device including a base having a channel, the channel having a sensing section, a sensing element arranged in the sensing section, and two electrodes electrically and respectively connected to two ends of the sensing section; the sensing method comprising the following steps:
  forming at least one microstructure, which is consisting of a plastic material without surface electric charge, in the sensing section, wherein a plurality of ions migrate to a surface of the at least one microstructure to form a field-induced electrical double layer when the surface of the microstructure has been polarized by an electric field, wherein the base comprises an upper substrate and a lower substrate, one of the upper substrate and the lower substrate being formed with a band-like groove, such that the band-like groove forms the channel when the upper substrate and the lower substrate are assembled together, wherein the upper and the lower substrate are made of the plastic material;
  preparing a noble metal nanoparticle layer and coating the noble metal nanoparticle on an outer surface of the sensing element;
  supplying an analyte-containing solution into the channel;
  providing an incident light and coupling the incident light into the sensing element;
  inputting a high-frequency alternating-current (AC) signal via the two electrodes to make a plurality of induced charges not neutralized and the field-induced electrical double layer maintained; and
  detecting an emergent light from the sensing element.

21. The sensing method as claimed in claim 20, wherein the sensing element is selected from the group consisting of a optical fiber element and a planar waveguide component.

22. The sensing method as claimed in claim 21, wherein the optical fiber element is a section of an optical fiber with a portion of a surface protective layer and a portion of a cladding layer thereof being stripped therefrom.

23. The sensing method as claimed in claim 20, wherein the microstructure is an embossed structure having a length or width between 0.1 mm and 1.0 mm.

24. The sensing method as claimed in claim 23, wherein the embossed structure is selected from the group consisting of a relief-like structure and a wedge-shape microstructure.

25. The sensing method as claimed in claim 20, wherein the microstructure is formed by a manner selected from the group consisting of ultraviolet-lithography galvanoformung abformung (UV-LIGA), printing, and ablating.

26. The sensing method as claimed in claim 20, wherein the microstructure has a height between 10 μm and 1000 μm.

27. The sensing method as claimed in claim 20, wherein the noble metal nanoparticle layer contains a type of noble metal nanoparticles selected from the group consisting of gold nanoparticles, silver nanoparticles, and other functionalized noble metal particles.

28. The sensing method as claimed in claim 20, wherein the high-frequency alternating-current (AC) signal leads the formation of circular vortices in the solution at corners of the microstructure.

29. The sensing method as claimed in claim 20, wherein, in the step of detecting the emergent light, changes in a signal of localized plasmon resonance (LPR) on the sensing element is measured, and the signal can be generated by any evanescent wave-based sensing means.

\* \* \* \* \*